United States Patent [19]

Deutsch

[11] Patent Number: 4,656,025

[45] Date of Patent: Apr. 7, 1987

[54] QUANTITATIVE SCREENING ASSAY OF TUMOR GLOBULIN FROM GASTRIC JUICE

[76] Inventor: Emmanuel Deutsch, 469 Beacon St., Boston, Mass. 02115

[21] Appl. No.: 725,246

[22] Filed: Apr. 19, 1985

[51] Int. Cl.[4] ............................................. G01N 33/53
[52] U.S. Cl. ......................................... 424/7.1; 435/7; 424/9
[58] Field of Search ........................... 424/2, 3, 7.1, 9; 435/7

[56] References Cited

U.S. PATENT DOCUMENTS

| | | | |
|---|---|---|---|
| 3,960,827 | 6/1976 | Björklund | 424/85 |
| 4,219,539 | 8/1980 | Deutsch | 424/9 |
| 4,269,765 | 5/1981 | Matsula et al. | 424/85 |
| 4,447,545 | 5/1984 | DeFazi et al. | 435/7 |

FOREIGN PATENT DOCUMENTS

| | | | |
|---|---|---|---|
| 0158202 | 1/1983 | German Democratic Rep. | 424/9 |
| 0345116 | 4/1955 | Switzerland | 424/9 |

OTHER PUBLICATIONS

Meglasson et al., CA 98:123723u (1983), Identification & Significance of Glucokinase in Transplantable Insulinomus.
Jokinen et al., CA 103:103021g (1983), Synthesis of Human Immunoglob. In Vitro Comparison of 2 Assays.
Taniguchi et al., CA 103:209446q, Measurement of Human Serum Immunoreactive γ-glutamyltranspeptidase, (1985).

Sigma Chemical Co., Biochemical and Organic Compounds, 1983, pp. 464-467.

Primary Examiner—Glennon H. Hollrah
Assistant Examiner—D. L. Dinner

[57] ABSTRACT

A quantitative screening protocol for the assay of tumor globulin which is separated from gastric juice of human patients at risk for gastric cancer comprising a purification procedure by column chromatography to recover tumor globulin from the gastric aspirate followed by a quantitative detection procedure in which the tumor globulin antigen from gastric juice which has been enriched in the separation process. The enriched tumor globulin is tested by ELISA quantitative assay using avidin/biotin/horseradish peroxidase. The preferred column is in the form of agarose beads covalently linked to both of diethylaminoethyl groups and Cibacron Blue F3GA. The protocol of the invention provides an improved screening of at risk patients to obtain early diagnosis of gastric cancer which is an improvement of applicant's prior U.S. Pat. No. 4,219,539 granted Aug. 26, 1980. The sensitivity of the diagnostic method of applicant's aforesaid U.S. Pat. No. 4,219,539 is adequate to detect 250 nanograms/ml of gastric cancer juice antigen per ml of sample. The present ELISA method detects as little as 0.2 nanograms per ml of tumor IgG and suprisingly gastric cancer samples are at a higher level than in patients having normal gastric juice, e.g. varying from about 4 to about 33 nanograms of IgG per mg of protein which is concentrated by column chromatography.

2 Claims, 1 Drawing Figure

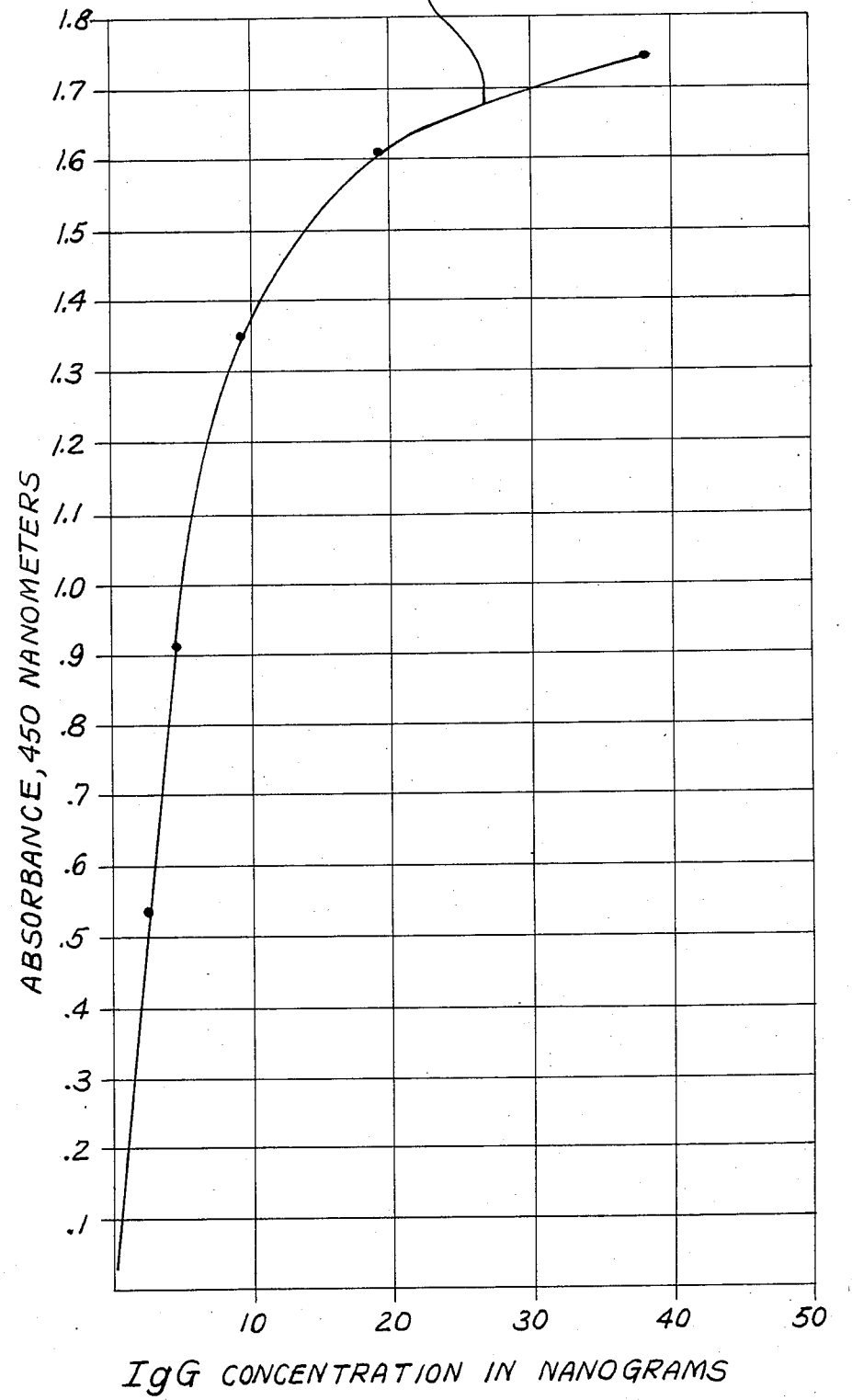

QUANTITATIVE SCREENING ASSAY OF TUMOR GLOBULIN FROM GASTRIC JUICE

BACKGROUND OF THE INVENTION

A. FIELD OF THE INVENTION

The invention is generally in the field of quantitative assay of gastric cancer in order to provide early diagnosis in differentiating between malignant and benign tumors of the gastric mucosae.

B. DESCRIPTION OF THE PRIOR ART

The antigen and the antibody which form a complex in the diagnosis of gastric cancer is described in my prior U.S. Pat. No. 4,219,539. This antigen, as described in my earlier patent, is reported in Cancer Research, Vol. 33, January 1973 and the antigen reacts immunochemically to give one precipitin line on double diffusion in agar gel. The qualitative test described in the patent is effective with concentrations of tumor globulin from gastric aspirate of the order of 250 micrograms per ml of samples taken from the gastric juice of the human patient at risk satisfies three additional diffusion criteria.

It is known in the prior art to employ separation procedures using chromatography in order to concentrate the protein antigen and thereby obtain greater sensitivity for a quantitative assay using enzyme linked immunosorbent assay which is hereinafter referred to as ELISA.

The U.S. Pat. No. 4,269,765, to Matsuda, describes a method of preparing specific immune serum from the fluids of cancer patients useful in diagnosis of cancer in which peritoneal fluid from stomach cancer patients is adjusted to pH 5.5 and purified on a column of diethylaminoethyl (DEAE) cellulose which is equilibrated at pH 5.5 with 0.2 M acetate buffer. In contrast to this acid pH procedure (5.5) and in contrast to the electrofocussing used by Matsuda et al, the present invention concentrates on an agarose buffer at a pH 8 with dipotassium acid phosphate buffers. The exchange resin in the present invention is an anion exchange resin of agarose and the fractionation accomplished after discarding the first fraction and eluting the absorbed protein with a small volume of buffered phosphate of pH 8 in the presence of increasing quantities of salt (0.1 molar up to 0.2 molar) results in a purification of at least 10 to 20 fold and up to 80 fold.

The U.S. Pat. No. 3,960,827, to Björklund, shows a procedure for purifying a cancer associated polypeptide antigen employing various molecular sieve type gels in bead form such as polyacrylamide gels, dextran gels and agarose gels which are equilibrated with suitable buffer at pH above 7.0. In the examples of the gels given in this patent none of these are gels having covalently linked groups of diethylaminoethyl. Further the technique of Björklund is to select an isolectric adjustment of the pH in order to precipitate the protein. To accomplish this precipitation a pH gradient is created which is tested. This complex procedure for purification is avoided in the present invention by the use of a covalent linked agarose beads having diethylaminoethyl groups attached and in the best embodiment also having Cibacron Blue F3GA dye attached.

It is known to use peroxidase as a label for use in ELISA and examples of purification of protein followed by ELISA assay have been described in the patent literature in DeFazio, et al, U.S. Pat. No. 4,447,545 for bladder cancer detection.

DeFazio et al describe a screening of the at risk population and a detection method in which a particular protein, called CRP protein found in inflammatory disease and in metastatic cancer can be recovered from bladder cancer patients. A first step is to collect urine and to separate bladder cancer protein on a chromatographic column in which the absorbent is hydroxyapatite. Two separate fractions are eluted at different phosphate levels. The second fraction was tested against anti-CRP, an anti-serum which is (Commercially available from Miles Laboratory) in immunoelectrophoresis, at pH 8.2 in an agarose gel. In contrast, the present invention uses an anion exchange beaded agarose chromatographic column covalently linked to DEAE and preferably also to Cibacron Blue F3GA.

The second step in DeFazio is an ELISA quantitative assay.

It is also known in Muroi, et al, U.S. Pat. No. 3,725,075, to use increasing sodium chloride concentrations for elution to separate proteins. This patent is of interest for the general teaching of the principles of protein separation at optimum pH.

It is noted that the protein purification taught by DeFazio, et al, U.S. Pat. No. 4,447,545, is based upon the recovery of a much larger amount of protein which is characteristic of bladder cancer in humans than the amount of protein present in gastric juice.

OBJECTS OF THE INVENTION

An object of the invention is to provide a new enrichment procedure for purifying tumor globulin associated with gastric cancer and recovered from aspirated cancer juice collected from patients by the procedure set forth in my prior U.S. Pat. No. 4,219,539 in order to create a quantitative assay for the enriched protein which is a gastric cancer tumor globulin after which an ELISA test is carried out to provide a sensitivity of detection of the tumor globulin down to about 1 nanogram per ml in the gastric juice of the patient.

A further object of the invention is to provide a standard for detection of very small concentrations in ranges based upon the enriched proteins wherein an enzyme linked immunosorbent assay is used to relate the amount of tumor IgG recovered from the enlarged protein chromatographic purification on the special beaded agarose and anion exchange resin having diethylaminoethyl groups attached thereto and preferably also having Cibacron Blue F3GA also attached by a covalent link. The value expressed in nanograms of IgG per microgram of protein present in the purified product from chromatographically recovered from the gastric juice is at least 3 to 4 times as great as the value which is found in testing normal gastric juice from patients in which there is no cancer diagnosis by the same procedure. In fact the testing of normal patients shows a large number of samples in which there is no IgG test obtained, a 0 value which is not registrable on the ELISA test and in all cases, the normal IgG level is expressed per mg of protein recovered is less than 2.0 nanograms IgG per mg of protein and in no case less than 1 IgG per mg of protein. The test is sensitive to detect between 0.05 nanograms per ml and 0.10 nanograms per ml.

Other and further objects will become apparent from the more detailed description which follows and from the examples providing the preferred procedures.

SUMMARY OF THE INVENTION

In my U.S. Pat. No. 4,219,539 I have described a simple test on an Ouchterlony plate which uses the collected gastric juice sample against an anti-IgG and anti-Fc to find the double precipitant line in the first immunodiffusion, this precipitant line having a sinuous characteristic which indicates complex formation. Some instances occur where the double precipitant line on a suspected cancer patient is not observed thereby making desirable a more sensitive test which requires the purification or concentration of the cancer or tumor globulin in the gastric juice. This is accomplished in the present invention by combining the steps of special column chromatography using beaded agarose to which diethylaminoethyl groups are covalently attached whereby a purification of at least 10 to 20 fold of the protein is achieved the bound protein being diluted with increasing salt concentrations from 0.1 molar to 0.2 molar. The purified protein is then tested by a very sensitive enzyme linked immunosorbent assay (ELISA). The assay is capable of detecting as little as 0.1 nanograms of IgG per mg of protein. Patients who have a positive diagnosis of gastric cancer have values of IgG per mg of protein varying from 4.4 to 33 while patients having no diagnosis of cancer have assay values less than 2.0 nanograms per mg of protein.

The gastric aspirate is dialyzed against 0.02 M $K_2HPO_4$, pH 8. The dialyzed juice is chromatographed on an ion exchange resin made up of beaded agarose which has both Cibacron Blue F3GA and diethylaminoethyl groups covalently attached to it. After the breakthrough fraction is collected, the starting buffer is made 0.1 M to 0.2 M in NaCl and a second fraction which contains the gastric cancer tumor globulin, is collected. This fraction is dialyzed against phosphate buffered saline (PBS) and lyophilized. Prior to analyses the lyophilate is reconstituted with 0.05 M sodium barbital buffer to a protein concentration of 10 mg/ml. Immunoelectrophoresis is performed on the reconstituted lyophilate against antisera to gastric tumor globulin. An anodic arc in the region $\alpha_1$-$\beta_2$ is considered a positive test.

An ELISA test which has been developed for the amplified gastric tumor globulin uses avidin-biotin, horseradish peroxidase to measure low levels of gastric tumor globulin as low as 0.1 to 0.2.nanograms/mgm of protein.

The high affinity of avidin for biotin, combined with the ease with which biotin conjugates to tumor globulin, results in extremely sensitive assays.

Avidin is a basic glycoprotein with a molecular weight of 68,000. Its name comes from the fact that its affinity for biotin is so high—about one million times greater than most antibody-antigen bonds and the avidin-biotin bond is essentially irreversible.

Biotin, with a molecular weight of about 274, easily conjugates to proteins without altering the biological activity of the proteins.

In the present test using the avidin-biotin binding, horseradish peroxidase is biotinylated. The avidin is incubated with the biotin-peroxidase at a precise ratio so that a three-dimensional complex is formed. Nine horseradish peroxidase molecules are held together by 3 avidin molecules leaving one biotin binding site open which detects tumor protein in the presence of a chromogen substrate.

DESCRIPTION OF THE DRAWING

The attached drawing shows the calibration curve for the ELISA test carried out for the invention, the X axis showing the IgG concentration in nanobrams and the Y axis showing the absorbants at 450 Nanometers.

DESCRIPTION OF THE PREFERRED EMBODIMENT

The quantitative screening assay of tumor globulin from gastric juices follows in general the sampling procedure of my prior U.S. Pat. No. 4,219,539, granted Aug. 26, 1984 but includes the following additional quantitative steps:

1. Collection of gastric cancer juice through a nasagastric tube and also through an endoscope during gastroscopy.
2. Dialysis against 0.005 molar TRIS buffer to eliminate impurities.
3. Fractionation of gastric juice associated proteins on a beaded agarose column having diethylaminoethyl groups covalently attached* or with additional Cibacron Blue F3GA also covalently attached.* 1 Gram of agarose is used per mg of globulin chromatographed. A flow rate of about 5 to 10 ml per hour is used.

*Both materials are supplied by BioRad Company, Richmond, Calif.

4. Removing first fraction, discarding and collecting cancer tumor globulin in a volume of approximately 6 milliliters from which the second fraction is formed.
5. Dialyzing the second fraction from step 4 against phosphate buffered saline and performing a quality control test on lyophilate in which there is recovered about 200 microliters of tumor globulin for carrying out the ELISA test.
6. ELISA test for low tumor globulin values using AvidinBiotin and horseradish peroxidase in the presence of 5-aminosalicylic acid as the chromogen substrate.

COLLECTION OF GASTRIC CANCER JUICE THROUGH A NASAGASTRIC TUBE AND ALSO THROUGH AN ENDOSCOPE DURING GASTROSCOPY

Following the procedure in my U.S. Pat. No. 4,219,539, a fiberoptic gastroscope is used for multiple biopsy and gastric juice specimens are collected through a nasagastric tube and also through the endoscope during gastroscopy from a fasting patient. The first portion of the fasting specimen is discarded and an adequate portion of gastric juice is collected which is brought to an alkaline pH by adding 5% sodium bicarbonate intragastrically which inactivates pepsin. The collected sample (about 25–50 ml) is dialyzed for 3 to 5 days against 0.005 M TRIS and the dialysis is carried out in the refrigerator with two changes of dialyzing buffer. The sample is then lyophilized and if desired can be stored in frozen condition until it is used. Ten mgs. of the lyophalate is solubilized in 0.5 mg of B-2 Barbital buffer (see Vol. II, Appendix II, Page 372 of the textbook "Methods in Immunology and Immunochemistry" edited by Williams and Chase, Academic Press, 1968. TRIS is a buffer made from tris (Hydroxymethyl) aminomethane and is described in Vol. II, Appendix II, Page 638, "Methods in Immunology and Immunochemistry".

FRACTIONATION OF GASTRIC JUICE ASSOCIATED PROTEINS BY ANION EXCHANGE COLUMN CHROMATOGRAPHY

The dialyzed product in Step 2 above which is dialyzed against 0.02 M $K_2HPO_4$ at pH 8 is passed through an anion exchange resin composed of agarose beads which has been treated to covalently bond diethylaminoethyl groups and Cibacron Blue F3GA dye to the beaded agarose. The aqueous solution of the gastric aspirate so dialyzed passes through the aforesaid chromatographic column and a first fraction known as Fraction A is collected and discarded. It is the second fraction B which is taken off of the column which constitutes the tumor globulin.

The concentration of sodium chloride in the starting buffered solution of 0.02 M $K_2HPO_4$ is changed from an NaCl concentration of 0.1 M up to 0.2 M and the buffer is passed through the column to elute a second fraction which constitutes the more concentrated tumor globulin fraction recovered from the gastric aspirate. This fraction B is then used as the sample material for the ELISA test.

ELISA TEST FOR LOW TUMOR GLOBULIN VALUE

The ELISA test is preferably a Micro ELISA test which is especially engineered for precision reproducibility and accuracy with very small levels of recovered tumor protein. Such Micro ELISA test systems in the art are available from a number of manufacturers and these test systems utilize specially manufactured microtiter plates adapted to receive small samples fabricated from plastic material which is inert or nonreactive to the reagents used in the testing system. Further the systems used lend themselves to optical scanning by the use of special scanning devices which are adapted to measure absorbency in the ultra-violet range. One supplier of ELISA material is Bio-Rad Laboratories of Richmond, Calif. Another supplier is Cappel Laboratories, a Division of Cooper Diagnostics Inc. of West Chester, Pennsylvania. A third supplier is Miles Scientific, a division of Miles Laboratories, Inc. of 30 West 475 North Aurora Road, Naperville, Ill. 60566.

There are many suppliers in Europe whose products are sold in the United States. The equipment used for reading the results, e.g. the optical apparatus, is manufactured by Dynatech Laboratories, 900 States Lane, Alexandria, Virginia 22314. Thus the reagents, the equipment and the laboratory dishes for the Micro ELISA method have all been worked out for the peroxidase substrates for a wide variety of chromogens and it is recognized that the micro ELISA method can be used to detect very small quantities of protein.

Dynatech Laboratories point out the need to provide optimal conditions using the reference reagents which must be strictly adhered to to achieve reproducibility. A first critical consideration is the buffer. A second critical consideration is the stability of the conjugated enzyme. Still another critical consideration is the incubation time, the temperature, the concentration of reactants and the emphasis on maintaining the conditions to assure reproducibility. Finally, consistent visual results in the wells must be correlated with photometric readings. In this connection the choice of the chromogen is important. The selected chromogen in the present case was 5-aminosalicylic acid. Another chromogen is diamino benzidine. Still another chromogen is (2-2' azino-di-(3 ethyl benzothiazolin sulfone-6)(diammonium salt). Still another chromogen is o-phenylenediamine (OPD).

In the present application any of these chromogens can be used since each is adapted under certain known conditions for best performance. The testing which was done herein was done for 5-aminosalicylic acid as the chromogen but earlier testing was done using 3,3',5,5',tetramethyldiaminobenzidine as the chromogen.

TESTING IN HUMAN PATIENTS

REPORT ON THE IMMUNOGLOBULIN G LEVELS IN JAPANESE CANCER SAMPLES

Gastric juice lyophilates obtained from gastric cancer patients were supplied by T. Norobu, MD & DDS, Director, Chiba Cancer Center, Chiba, Japan. 5 to 7 mg of the lyophilates were dissolved in 0.01 M sodium phosphate, 0.15 M sodium chloride, pH 7.2. Protein content of the dissolved lyophilates (which were in a total volume of 1 ml) was assayed by the Coomassie dye binding method (1) "Instruction Manual for Bio-Rad Protein Assay, Bio-Rad Laboratories, Richmond, Calif. 1981". The protein ranged from 0.5 to 5.8 mg/ml. Immunoglobulin G assay was performed by the ELISA (Enzyme linked immunoassay) method given by Miles Scientific, Naperville, Illinois (2) "Product Profile 1984 Peroxidase conjugated antisera, Miles Scientific, Naperville, Illinois". The procedure was a direct assay which uses anti IgG coupled to horseradish peroxidase. The substrate (chromogen) was 5-aminosalicylic acid. The reaction was carried out in microtiter plates and the individual wells (after color developed) were optically read using the Dynatech Optical scanner (Dynatech Laboratories, Alexandria, Virginia). The range of human IgG in the gastric juice samples were determined from a calibration curve shown in FIG. 1. The levels in the curve were from 2 ng to 38 ng.

COLLECTION AND COLUMN CHROMATOGRAPHY

1. Collection of gastric cancer juice through a nasagastric tube and also through an endoscope during gastroscopy.
2. Dialysis against 0.005 molar TRIS buffer.
3. Fractionation of gastric juice associated proteins using a beaded agarose having Cibacron Blue F3GA* and diethylaminoethyl groups covalently attached.

*The formula for Cibacron F3GA is as follows:

4. Removing first fraction, discarding and collecting cancer tumor globulin.
5. Dialyzing second fraction against phosphate buffered saline and quality control test on Lyophilate.
6. ELISA test for low tumor globulin values using Avidin-Biotin and horseradish peroxidase in the presence of 5-aminosalicylic acid as the chromogen substrate.

The above procedure has been changed to reflect the Miles Scientific Micro ELISA method.

The IgG reagents available from Miles for detecting IgA was Code No. 61-130, Human IgG, titer 1:1500; or Code No. 61-230, Human IgG, titer 1:2500.

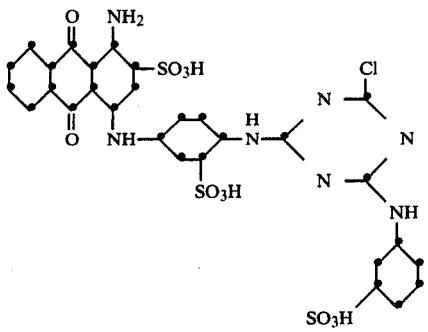

This dye is also known as Procion-ICI, Cibacron Ciba introduced in 1957. Procion ICI is a trade name of Imperial Chemical Industries in England. Cibacron is a trade name of the Ciba Company in Switzerland. The Cibacron Blue dies of the 3G series were introduced in 1957 and have been widely used as reaction dyes for cellulose. The following method was used following the procedure by Miles for the Micro ELISA Method:

MICROELISA METHOD

Reagents:
1. Coating Buffer
   10 mM Phosphate Buffer pH 7.4
   150 mM NaCl
   1.1% Sodium Azide
2. Washing Buffer
   10 mM Phosphate Buffer pH 7.4
   150 mM Sodium Chloride
   0.05% (v/v Tween 20
3. Reaction Buffer
   0.02 M Sodium Phosphate, pH 6.8
4. Stop Buffer
   3M NaOH
5. 5-Amino Salicylic Acid
6. Hydrogen Peroxide Procedure:
1. Dissolve antigen in coating buffer, 20 μg/ml.
2. Pipette 0.2 ml of coating solution to each well of the polystyrene microtiter plate and incubate (covered) overnight at 4° C.
3. Remove the coating solution and wash three times with washing buffer.
4. Dilute the peroxidase conjugate in washing buffer. One may make individual or serial dilutions, but it is best to start at a dilution well below the expected titer, e.g. 1:50 or 1:100. Add 0.15 ml of diluted conjugate to each well.
5. Incubate at room temperature for 2 hours.
6a. During incubation, prepare the reaction solution. Dissolve 5-aminosalicylic acid 1 mg/ml in pre-heated reaction buffer at 56° C.
6b. Add approximately 1-5 mg activated charcoal to each 100 ml substrate. Mix and filter through Whatman No. 1 filter paper. This step removes excess color from the substrate solution.
6c. Prepare a fresh 1% peroxide solution in water and add 0.1 ml to each 10 ml of reaction substrate.
7. Following incubation (step 5), wash 3 times with washing buffer, at least 5 minutes per wash. Then rinse 3 times with distilled water.
8. Add 0.2 ml of freshly prepared $H_2O_2$/substrate solution to each well.
9. Stop the color reaction after 30 minutes with 0.1 ml of stop buffer.
10. Read adsorbance at 450 NM.

The results of the gastric cancer samples are given in Table 1. Normal gastric secretions were obtained from the Out Patient Department of the Carney Hospital, Dorchester, Massachusetts. The samples were dialyzed against phosphate buffered saline. The samples were not lyophilized and the protein content was measured with Coomassie dye as stated above. The protein contents ranged from 0.12 to 1.2 mg/ml. IgG levels in the normal samples were determined as described above. The results are given in Table 2.

TABLE 1

IMMUNOGLOBIN G LEVELS IN GASTRIC CANCER SAMPLES

| *Sample | IgG (ng/ml) | Protein (mg/ml) | IgG (ng/mg Protein) |
|---|---|---|---|
| 2-1 | 15 | 2 | 7.5 |
| 2-2 | 6 | 1.8 | 3.3 |
| 3-1 | 6.5 | 1.0 | 6.5 |
| 3-2 | 5.5 | 1.1 | 5.0 |
| 4-1 | 10 | 2.3 | 4.3 |
| 4-2 | 9 | 2.1 | 4.3 |
| 5 | 10 | 3.1 | 3.2 |
| 6-1 | 14.6 | 5.8 | 2.5 |
| 6-2 | 20 | 0.74 | 27 |
| 7-1 | 10.5 | 0.42 | 25 |
| 7-2 | 11.5 | 0.54 | 21.3 |
| 8-1 | 9.0 | 0.54 | 16.7 |
| 8-2 | 8.5 | 0.93 | 9.1 |
| 9-1 | 15 | 0.76 | 19.7 |
| 9-2 | 0.35 | 0.74 | 0.5** |
| 9-3 | 11.0 | 1.3 | 8.5 |
| 10-1 | 11.5 | 0.8 | 14.3 |
| 10-2 | 11.5 | 1 | 11.5 |
| 10-3 | 16.5 | 0.5 | 33 |
| 11-1 | 6.5 | 1.1 | 6 |
| 11-2 | 5 | 1 | 5 |
| 12-1 | 15 | 2 | 7.5 |
| 12-2 | 13.5 | 2.1 | 6.4 |
| 13-1 | 11.5 | 2.1 | 5.5 |
| 14-1 | 13.0 | 1.1 | 11.8 |
| 14-2 | 6.5 | 2 | 3.2 |
| 14-3 | 21 | 2 | 10.5 |
| 15-1 | 11.5 | 2.1 | 5.5 |
| 15-2 | 10.5 | 2.4 | 4.4 |

*The first number of the Sample is the patient identification, and the following number indicates the specimen, e.g. 9-1, 9-2, 9-3 indicate three specimens from patient 9.
**The low value obtained in 9-2 reflects a technical error and the test was repeated to give a result between 9-1 and 9-3.

TABLE 2

| Sample | IgG (ng/ml) | Protein (mg/ml) | IgG (ng/mg Protein |
|---|---|---|---|
| NGJ (Kelly) | 0.45 | 0.25 | 1.8 |
| NGJ (Sweet) | 0.40 | 0.25 | 1.6 |
| NGJ (Guerro) | 0 | 0.40 | 0 |
| NGJ (Fufari) | 0 | 0.37 | 0 |
| NGJ (Manning) | 0 | 0.12 | 0 |
| NGJ (Rizal) | 0.35 | 0.6 | 0.6 |
| NGJ (Smith) | 0.40 | 0.23 | 1.7 |
| NGJ (Duncan | 0.24 | 0.61 | 0.4 |
| NGJ (Boyle) | 0 | 1.1 | 0 |
| NGJ (Wilcewski) | 0 | 0.7 | 0 |
| NGJ (Malloy) | 0.45 | 1.2 | 0.4 |

I claim:

1. A process for the assay of cancerous gastric juice in a human patient comprising:
   (1) collecting a fasting gastric juice sample from a patient through a tube by first discarding the fasting sample and collecting about 25–50 ml of a further gastric juice sample to which alkali is added to raise the pH above 7 and inactivate pepsin;
   (2) dialyzing the gastric juice against 0.005 molar Tris buffer to remove interfering substances;
   (3) fractionating the dialyzed material in a beaded agarose chromatographic column having diethylaminoethyl groups covalently attached whereby the gastric juice associated cancer proteins are absorbed to the column and impurities are removed in a first fraction which is discarded;
   (4) removing the concentrated gastric juice associated protein by adding a buffered solution of 0.02 molar $K_2HPO_4$ in which an increase in concentration of NaCl of 0.1 molar up to 0.2 molar is added whereby a concentrated fraction is removed;
   (5) dialyzing the concentrated fraction with 0.02 molar $K_2HPO_4$ and 0.1 molar NaCl; and
   (6) performing an ELISA test using Avidin-Biotin and horseradish peroxidase in the presence of 5-aminosalicylic as the chromogen substrate to obtain a value of IgG based upon the amount of protein present in the sample, a value of IgG varying from 2.5 nanograms per mg of protein up to 33 nanograms per mg of globulin protein indicating an immunoglobulin G level which is presumptively diagnostic of gastric cancer.

2. A process as claimed in claim 1 wherein said agarose column is cross-linked to Cibacron F3GA by means of a covalent bond.

* * * * *